United States Patent [19]

Wilk

[11] Patent Number: 5,391,173
[45] Date of Patent: Feb. 21, 1995

[54] LAPAROSCOPIC SUTURING TECHNIQUE AND ASSOCIATED DEVICE

[76] Inventor: Peter J. Wilk, 185 W. End Ave., New York, N.Y. 10023

[21] Appl. No.: 195,749

[22] Filed: Feb. 10, 1994

[51] Int. Cl.⁶ .............................................. A61B 17/04
[52] U.S. Cl. .................................... 606/144; 128/898; 606/139; 606/232
[58] Field of Search ................ 606/139, 232, 144–148; 128/898; 24/115, 129 R, 130, 131 C, 324, 453, 129 W

[56] References Cited

U.S. PATENT DOCUMENTS

| | | |
|---|---|---|
| 3,166,072 | 10/1962 | Sullivan, Jr. .......................... 606/220 |
| 3,952,377 | 4/1976 | Morell ................................ 24/136 R |
| 4,060,089 | 11/1977 | Noiles ................................ 606/220 |
| 4,461,059 | 7/1984 | Burg .................................. 24/129 R |
| 4,532,926 | 8/1985 | O'Holla . |
| 4,534,350 | 8/1985 | Golden et al. . |
| 4,573,469 | 3/1986 | Golden et al. . |
| 4,644,953 | 2/1987 | Lahodny et al. . |
| 4,724,839 | 2/1988 | Bedi et al. . |
| 4,890,613 | 1/1990 | Golden et al. . |
| 4,919,370 | 4/1990 | Martin et al. ....................... 24/129 R |
| 4,932,960 | 6/1990 | Green et al. . |
| 5,059,206 | 10/1991 | Winters . |
| 5,258,015 | 11/1993 | Li et al. .................................. 24/453 |
| 5,306,290 | 4/1994 | Martins et al. ........................ 606/232 |

Primary Examiner—Stephen C. Pellegrino
Assistant Examiner—Gary Jackson
Attorney, Agent, or Firm—R. Neil Sudol; Henry D. Coleman

[57] ABSTRACT

A laparoscopic suturing method comprises the steps of (a) disposing a trocar sleeve in an abdominal wall of the patient, (b) moving a first end section of a suture through the trocar sleeve and into an abdominal cavity of the patient so that a second end section of the suture remains outside the patient, (c) passing the first end section of the suture through organic abdominal tissues of a patient, and (d) drawing the first end section of the suture back out through the trocar sleeve upon passing of the suture through the abdominal tissues of the patient. Upon drawing of the first end section of the suture out of the patient, a suture locking device is slid along the suture end sections and through the trocar sleeve until the locking device is substantially juxtaposed to the organic tissues at the opening. Then, the suture end sections are severed on a side of the locking device opposite the abdominal tissues and the opening. The locking device has a pair of channels with barbs pointed in one direction for preventing the suture end sections from being removed from the device.

27 Claims, 3 Drawing Sheets

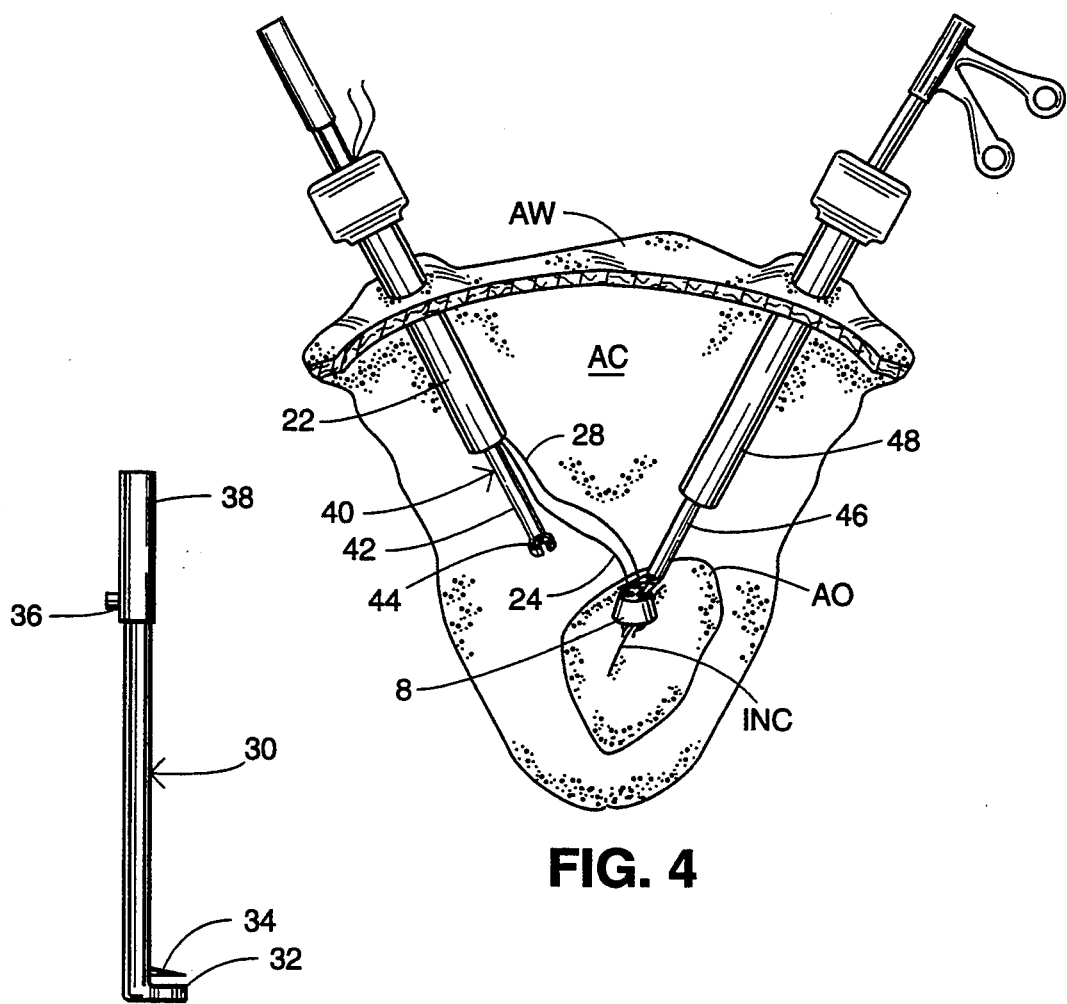
FIG. 4
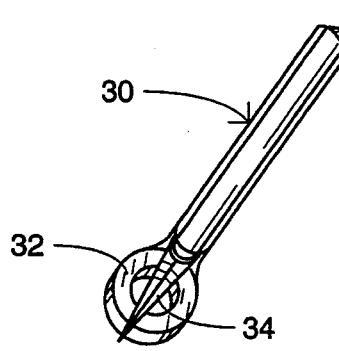
FIG. 3
FIG. 5
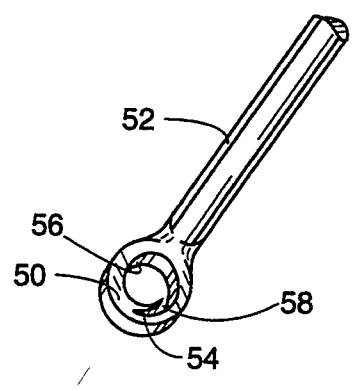
FIG. 6

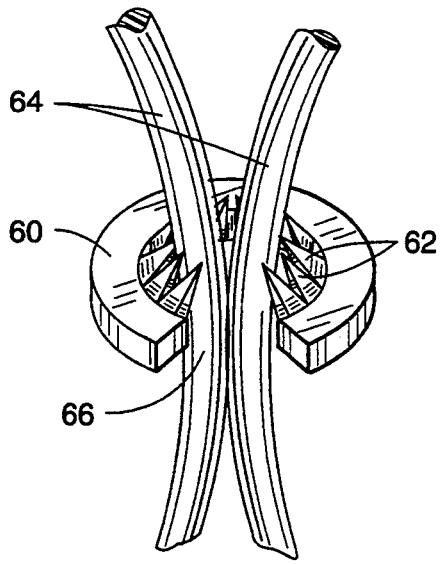
FIG. 7
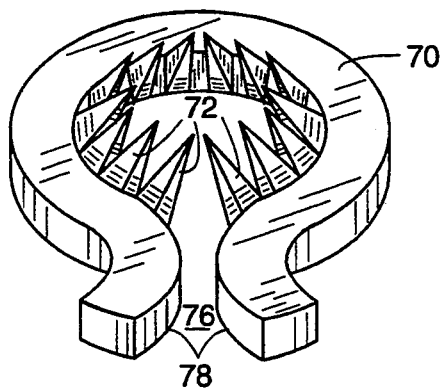
FIG. 8
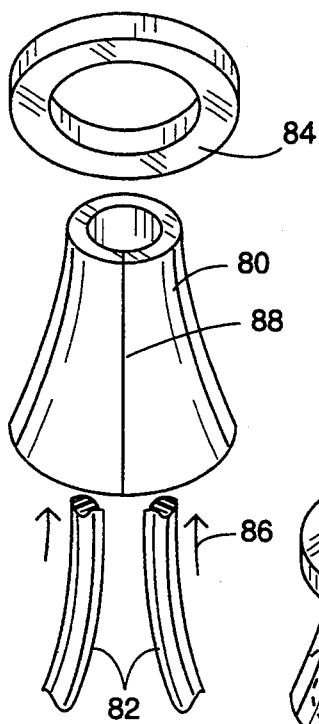
FIG. 9A
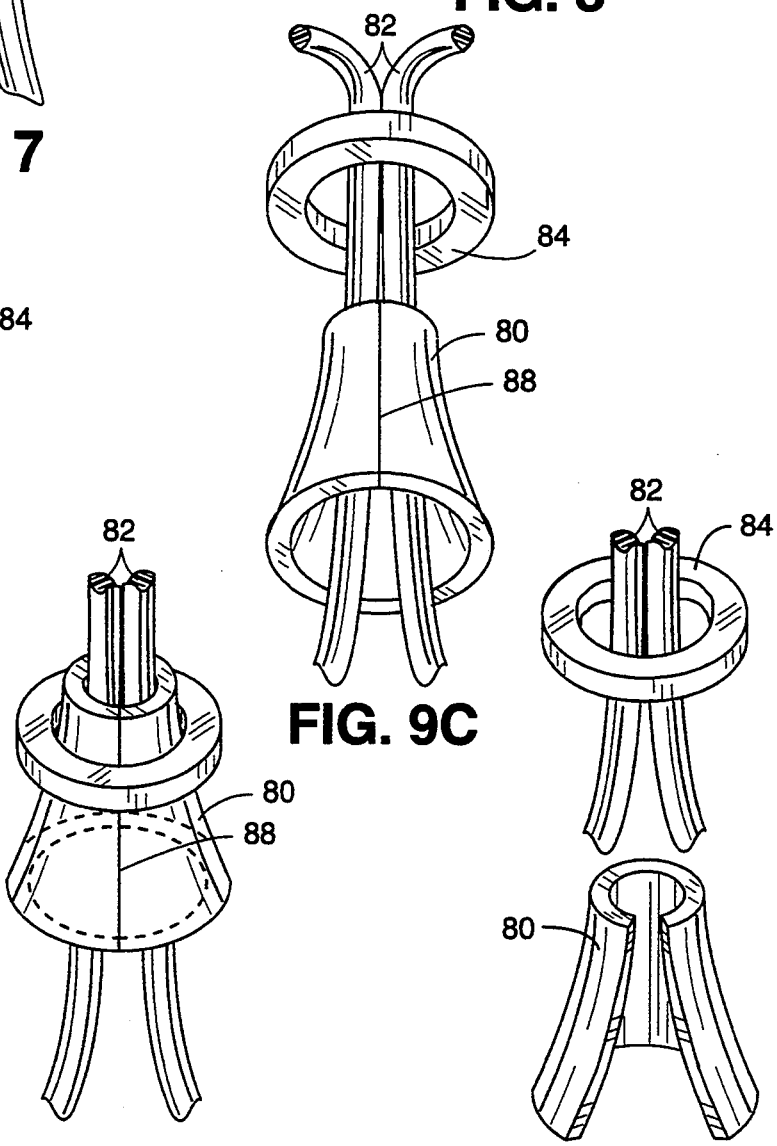
FIG. 9B  FIG. 9C  FIG. 9D

LAPAROSCOPIC SUTURING TECHNIQUE AND ASSOCIATED DEVICE

BACKGROUND OF THE INVENTION

This invention on relates to a suturing technique. More particularly, this invention relates to a suturing technique of particular applicability to laparoscopic surgery. This invention also relates to an associated suture closure device.

Laparoscopic surgery is currently a rapidly spreading innovative medical technique. In laparoscopic surgery, internal organs of the patient are operated upon through a plurality of sleeves inserted in the abdominal wall of the patient. The progress of the operation is continuously monitored by the surgeon and assisting personnel with the aid of a specialized camera device called a laparoscope. The laparoscope is itself inserted into the patient through one of the sleeves in the abdominal wall. The action of the distal ends of laparoscopic instruments on the internal tissues of the patient is observed on one or more television monitors connected to the laparoscope.

One of the drawbacks of laparoscopic surgery is the inability to effectively form sutures.

OBJECTS OF THE INVENTION

An object of the present invention is to provide a new technique for forming sutures.

Another object of the present invention is to provide such a technique which can be used in laparoscopic surgery.

A further object of the present invention is to provide a device for use in quickly locking a suture.

A more particular object of the present invention is to provide such a device which can be used in laparoscopic operations.

These and other objects of the present invention will be apparent from the drawings and detailed descriptions herein.

SUMMARY OF THE INVENTION

A device for locking a suture comprises, in accordance with the present invention, a body member made of biocompatible material and provided with a passageway for receiving a suture. The body member is further provided along the passageway with barbs or other, equivalent, elements for preventing a suture from passing in a first predetermined direction along the passageway while allowing the suture to slide relative to the body member in an opposite direction through the passageway.

According to another feature of the present invention, the body member tapers down in the direction of slidability of a suture through the passageway. The passageway itself may be tapered from that direction.

The body member may take the form of a slotted ring provided with flared extensions at the slot for facilitating a lateral insertion of a suture into the ring.

A suturing method in accordance with the present invention utilizes this device to close or lock a suture. Upon a passing of the suture through organic tissues of a patient so that two strands of the suture extend from the organic tissues on opposite sides of an opening in the tissues, at least one of the strands is inserted into the passageway. The other strand is either pre-inserted through the device or is threaded through the device at this juncture. Then, the locking device is slid along the two strands until the locking device is substantially juxtaposed to the organic tissues at the opening in the organic tissues of the patient, thereby drawing the strands together and locking the strands in a tightened closure configuration. The strands are then severed on a side of the locking device opposite the organic tissues and the opening.

In one embodiment of the locking device in accordance with the present invention, the body member is provided with a pair of substantially parallel passageways or channels, each of the channels being provided with barbs or other locking elements for preventing a suture from passing in the first predetermined direction along the respective channel while allowing the suture to slide relative to the body member in the opposite direction through the respective channel. In that event, one suture strand or end section is inserted through one channel of the locking device and the other strand or end section is inserted through the other channel. It is possible, however, to provide the locking device with one channel or passageway, both strands of the suturing device being inserted through that passageway.

A laparoscopic suturing method comprises, in accordance with the present invention, the steps of (a) disposing a trocar sleeve in an abdominal wall of a patient, (b) moving a first end section of a suture through the trocar sleeve and into an abdominal cavity of the patient so that a second end section of the suture remains outside the patient, (c) passing the first end section of the suture through organic abdominal tissues of the patient, and (d) drawing the first end section of the suture back out through the trocar sleeve upon passing of the suture through the abdominal tissues of the patient. Upon drawing of the first end section of the suture out of the patient, the locking device described above is slid along the suture end sections and through the trocar sleeve until the locking device is substantially juxtaposed to the organic tissues at the opening. Then, the suture end sections are severed on a side of the locking device opposite the abdominal tissues and the opening.

According to another feature of the present invention, the step of sliding includes the steps of (i) providing an elongated instrument, (ii) inserting a distal end portion of the elongate instrument through the trocar sleeve, and (iii) pushing the locking device along the suture end sections by engaging the locking device with the distal end portion of the instrument.

Where the laparoscopic pushing instrument is provided at a distal tip of the distal end portion with a cutting edge, the severing of the suture end sections includes the step of manipulating the instrument and the suture from outside the patient so as to bring the suture end sections at the locking device into contact with the edge.

Where the instrument is provided at a distal tip of the distal end portion with an aperture smaller than the locking device, the method further comprises the step of passing the first end section and the second end section through the aperture prior to insertion of the distal end portion of the instrument through the trocar sleeve.

A laparoscopic instrument comprises, in accordance with the present invention, an elongate shaft, means at a distal end of the shaft defining an aperture, and a cutting edge attached to the instrument at the distal end along the aperture.

BRIEF DESCRIPTION OF THE DRAWING

FIG. 3 is a side elevational view of a laparoscopic instrument shown in use in FIG. 2C, for applying the locking device of FIG. 1.

FIG. 4 is a schematic cross-sectional view similar to FIGS. 2A-2C, showing a step performable between the step of FIG. 2C and the step of FIG. 2D.

FIG. 5 is a partial schematic perspective view of the laparoscopic instrument of FIGS. 2C and 3, showing a cutting edge in accordance with the present invention.

FIG. 6 is a partial schematic perspective view, showing a modification of the instrument of FIGS. 2C, 3, and 5.

FIG. 7 is a schematic perspective view, on an enlarged scale, of another locking device in accordance with the present invention, showing two strands of a suture inserted through the locking device.

FIG. 8 is a schematic perspective view, on a substantially enlarged scale, of a further locking device in accordance with the present invention.

FIG. 9A is a schematic exploded perspective view of a suture locking device, suture strands and a suture threading device in accordance with the present invention.

FIG. 9B is a schematic perspective view of the suture locking device, suture strands and the suture threading device of FIG. 9B, showing the suture strands inserted through the threading device which in turn is inserted through the locking device.

FIG. 9C shows a step in a suture insertion operation subsequent to a step shown in FIG. 9B.

FIG. 9D shows another succeeding step in a suture insertion operation subsequent to the step shown in FIG. 9C.

DETAILED DESCRIPTION

Figure 1:
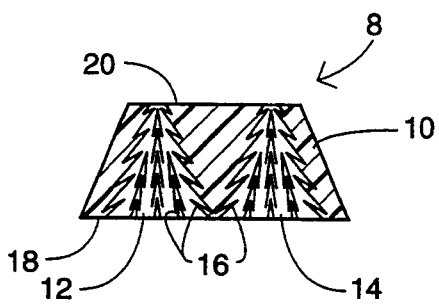
FIG. 1 is a schematic longitudinal cross-sectional view, on an enlarged scale, of a suture locking device in accordance with the present invention.

As illustrated in FIG. 1, a device 8 for locking a suture comprises a body member 10 made of biocompatible material and provided with two substantially parallel passageways or channels 12 and 14. Each passageway or channel 12 and 14 is lined with barb-like protuberances 16 pointed generally towards one end of the respective passageway 12 and 14. During use of locking device 8, a suture end (not shown in FIG. 1) is passed through a passageway 12 or 14 from one side 18 of device 8 towards an opposite side 20 thereof. Barb-like protuberances 16 serve to prevent the suture from moving in the opposite direction from side 20 to side 18, while allowing suture insertion in the opposite direction along the respective passageway. It is to be noted that device 8 may also work if just one passageway is provided (see FIGS. 7-9D).

As further illustrated in FIG. 1, body member 10 is tapered in a direction from side 18 to side 20. Likewise, passageways 12 and 14 each taper down in the same direction to facilitate insertion of a suture thread in the proper direction through the passageways.

Figure 2A:
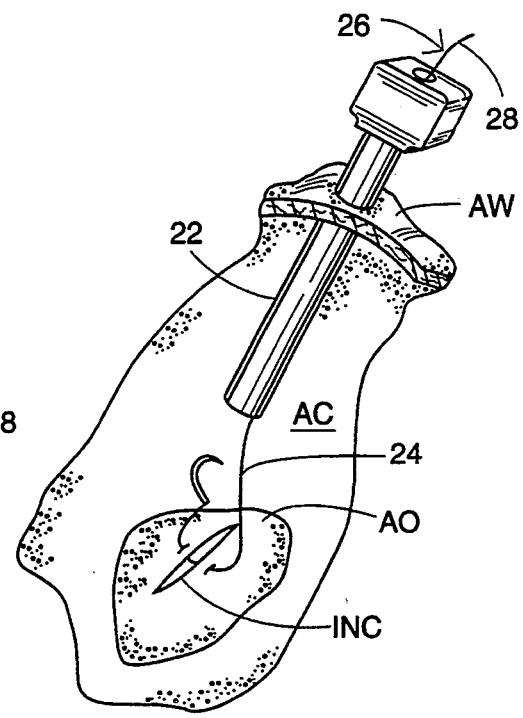
FIGS. 2A-2C are schematic cross-sectional views of a patient's abdomen, showing successive steps in a laparoscopic suturing procedure utilizing the device of FIG. 1.

As depicted in FIGS. 2A-2D, in a laparoscopic suturing procedure, a trocar sleeve 22 is disposed in an abdominal wall AW of the patient. A first end section or strand 24 of a suture 26 is moved through trocar sleeve 22 and into an abdominal cavity AC of the patient while a second end section or strand 28 of the suture remains outside the patient. As illustrated in FIG. 2A, first end section 24 of suture 26 is passed through tissues of an abdominal organ AO of the patient, for example, through the use of an arcuate needle as disclosed in U.S. Pat. No. 5,281,234, the disclosure of which is hereby incorporated by reference. More particularly, first end section 24 of suture 26 is passed through an incision INC in abdominal organ AO. Subsequently, first end section 24 is brought back out through trocar sleeve 22 (FIG. 2B) and passed through one passageway 12 or 14 of locking device 8.

Second end section 28 of suture 26 is inserted through the other passageway 14 or 12 of device 8, either before or after the passing of end section 28 therethrough. Alternatively, locking device 8 may be pre-attached to suture 26 along end section 28. In that case, only the first end section 24 need be threaded through device 8 during a laparoscopic operation.

Figure 2B:
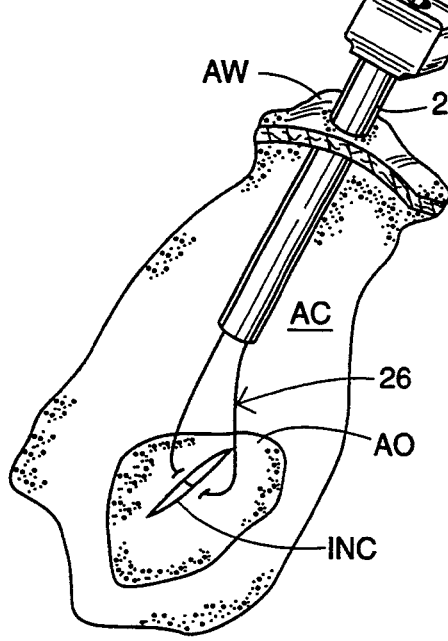
Figure 2C:
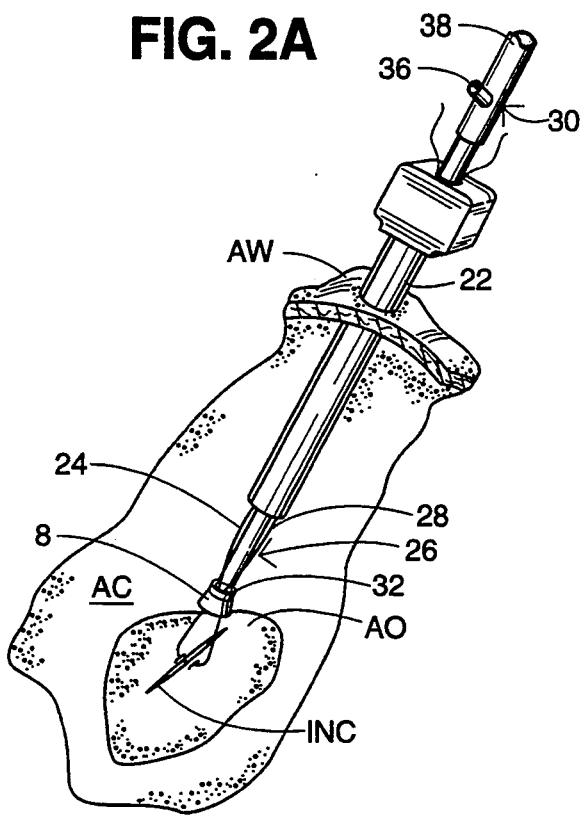
Figure 2D:
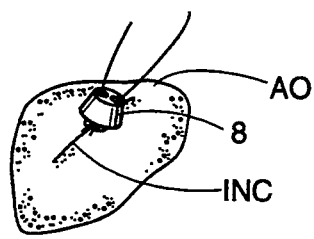
FIG. 2D is a schematic perspective view of an organ and an incision or wound closed by a suture which is locked by the device of FIG. 1, in accordance with the present invention.

As illustrated in FIG. 2B, both suture end sections or strands 24 and 28 are inserted through locking device 8 outside of the patient. Then, as depicted in FIG. 2C, an elongate laparoscopic instrument 30, provided at a distal end with a transversely extending ring 32 (see FIG. 3), is used to push locking device 8 along suture end sections 24 and 28 and through trocar sleeve 22 into abdominal cavity AC until the locking device is substantially juxtaposed to organ AO at incision or opening INC. Then, suture end sections 24 and 28 are severed on a proximal side of locking device 8, opposite abdominal organ AO and incision INC (FIG. 2D).

In sliding locking device 8 along suture end sections 24 and 28, distal ring 32 of instrument 30 is inserted through trocar sleeve 22 and engages locking device 8 along the proximal side 20 thereof. As illustrated in FIGS. 3 and 5, pushing instrument 30 may be provided at a distal tip with a pair of scissors 34 or other movable cutting element which is operatively connected to an actuator button 36 on a handle 38 of the instrument. Upon a sliding of locking device 8 to the abdominal organ AO, button 36 is pressed to close the scissors or cutting element 34 to sever suture end sections 24 and 28. FIG. 5 shows scissors in a closed, cutting configuration. During a sliding of locking device 8 along suture end sections 24 and 28, scissors 34 are opened and spaced from the end sections 24 and 28.

In a modification of the above-described procedure, shown in FIG. 4, a pushing instrument 40 is used which has an elongate shaft 42 provided at a distal end with a slotted ring 44. Upon a juxtaposition of the locking device 8 with the abdominal organ AO under repair, instrument 40 is manipulated from outside the patient to remove suture end sections 24 and 28 from the ring (see FIG. 4). A laparoscopic scalpel or scissors 46 inserted into the abdomen through another trocar sleeve 48 is then operated to sever the suture end sections 24 and 28 at the proximal side of the locking device 8.

As illustrated in FIG. 6, a guide ring 50 extending in a substantially transverse plane at the distal end of a laparoscopic instrument shaft 52 may be provided with a fixed cutting edge 54 which is reached by a suture only upon manipulating the suture and the instrument to pass the suture from a main guide aperture 56 and through a labyrinthine type slot 58. The labyrinthine slot 58 prevents inadvertant severing of a suture during an insertion of locking device 8.

It is to be noted that aperture 56 in the instrument of FIG. 6, as well as the corresponding guide apertures in other pushing instruments disclosed herein, is smaller that the proximal side 20 of locking device 8.

As illustrated in FIG. 7, another locking device utilizable with the method discussed above with reference to FIGS. 2A–2D and 4 takes the form of a ring 60 provided along an inner side with barbs 62 inclined in a common axial direction for purposes of preventing suture strands 64 from sliding relative to ring 60 in a direction opposite to the direction of inclination of barbs 62. Ring 62 is also provided with a slot 66 for enabling a lateral insertion of strands 64 into ring 62.

FIG. 8 shows a further locking device in the form of a ring 70 provided along an inner side with barbs 72 inclined in a common axial direction for purposes of preventing suture strands (not shown) from sliding relative to ring 70 in a direction opposite to the direction of inclination of barbs 72. Ring 72 is also provided with a slot 76 for enabling a lateral insertion of suture strands into ring 72. To further facilitate the insertion of a suture into ring 72, the ring is provided on opposite sides of slot 76 with outwardly flared lips or extensions 78.

As depicted in FIG. 9A, a substantially conical threading or guiding device 80 is provided for facilitating insertion of suture strands 82 through an annular suture locking device 84. Suture strands 82 are inserted in the direction of arrows 86 into threading device 80 upon an insertion of a tapered end of that device into locking device 84, as illustrated in FIG. 9B. Subsequently, after threading of suture strands 82 completely through device 80, the threading device is removed from locking device 84, as illustrated in FIG. 9C. The threading device 80 is provided with a slot 88, whereby that device may be opened to enable removal from suture strands 82, as shown in FIG. 9D. Locking device 84 is provided with non-illustrated barbs. Threading device 80 is made, at least along an outer surface, of a material which resists penetration by the barbs of locking device 84, thereby enabling withdrawal of the threading device 80 from locking device 84.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A suturing method comprising the steps of:
providing a suture;
providing a locking device made of biocompatible material and having at least one passageway for receiving said suture, said locking device being further provided along said passageway with means for preventing a suture from passing in a first predetermined direction along said passageway while allowing the suture to slide relative to said locking device in an opposite direction through said passageway;
passing said suture through organic tissues of a patient so that two strands of said suture extend from said organic tissues on opposite sides of an opening in said tissues;
inserting at least one of said strands into said passageway;
sliding said locking device along said two strands until said locking device is substantially juxtaposed to said organic tissues at said opening, thereby drawing said strands together and locking said strands in a tightened closure configuration; and
severing said strands on a side of said locking device opposite said organic tissues and said opening.

2. The method defined in claim 1, further comprising the steps of:
disposing a trocar sleeve in an abdominal wall of the patient;
moving a portion of said suture through said trocar sleeve and into an abdominal cavity of the patient, said organic tissues being located in said abdominal cavity, said step of moving being implemented prior to said step of passing; and
upon completion of said step of passing and prior to said step of inserting, bringing an end section of said one of said strands back out through said trocar sleeve.

3. The method defined in claim 2 wherein said step of sliding includes the steps of:
providing an elongate instrument;
upon insertion of said one of said strands through said passageway in said locking device, inserting a distal end portion of said elongate instrument through said trocar sleeve; and
pushing said locking device along said strands by engaging said locking device with said distal end portion of said instrument.

4. The method defined in claim 3 wherein said instrument is provided at a distal tip of said distal end portion with a cutting edge, said step of severing including the step of manipulating said instrument and said strands from outside the patient so as to bring said strands at said locking device into contact with said edge.

5. The method defined in claim 3 wherein said instrument is provided at a distal tip of said distal end portion with an aperture smaller than said locking device, further comprising the step of passing said two strands through said aperture prior to insertion of said distal end portion of said instrument through said trocar sleeve.

6. The method defined in claim 1 wherein said locking device is provided with a pair of substantially parallel channels, said passageway constituting one of said channels, each of said channels being provided with means for preventing said suture from passing in a first predetermined direction along the respective channel while allowing the suture to slide relative to said body member in an opposite direction through the respective channel, said step of inserting including the step of inserting said one of said strands through one of said channels in said opposite direction.

7. The method defined in claim 6, further comprising the step of inserting another of said strands through another of said channels.

8. A laparoscopic suturing method comprising the steps of:
disposing a trocar sleeve in an abdominal wall of a patient;

moving a first end section of a suture through said trocar sleeve and into an abdominal cavity of the patient so that a second end section of said suture remains outside the patient;

upon completion of said step of moving, passing said first end section of said suture through organic tissues of the patient;

upon completion of said step of passing, drawing said first end section of said suture back out through said trocar sleeve;

providing a locking device made of biocompatible material and having at least one passageway for receiving said suture, said locking device being further provided along said passageway with means for preventing said suture from passing in a first predetermined direction along said passageway while allowing said suture to slide relative to said locking device in an opposite direction through said passageway;

sliding said locking device along said first end section and said second end section and through said trocar sleeve until said locking device is substantially juxtaposed to said organic tissues at said opening;

severing said first end section and said second end section on a side of said locking device opposite said organic tissues and said opening.

9. The method defined in claim 8 wherein said step of sliding includes the steps of:
providing an elongate instrument;
inserting a distal end portion of said elongate instrument through said trocar sleeve; and
pushing said locking device along said first end section and said second end section by engaging said locking device with said distal end portion of said instrument.

10. The method defined in claim 9 wherein said instrument is provided at a distal tip of said distal end portion with a cutting edge, said step of severing including the step of manipulating said instrument and said suture from outside the patient so as to bring first end section and said second end section at said locking device into contact with said edge.

11. The method defined in claim 9 wherein said instrument is provided at a distal tip of said distal end portion with an aperture smaller than said locking device, further comprising the step of passing said first end section and said second end section through said aperture prior to insertion of said distal end portion of said instrument through said trocar sleeve.

12. The method defined in claim 9, further comprising the step of inserting said first end section and said section through said passageway prior to said step of sliding.

13. A suturing method comprising the steps of:
providing a suture;
providing a locking device made of biocompatible material and having at least one passageway for receiving said suture, said locking device being further provided with means for preventing a suture from passing in a first predetermined direction along said passageway while allowing the suture to slide relative to said locking device in an opposite direction through said passageway;
passing said suture around organic tissues of a patient so that two strands of said suture extend from said organic tissues on opposite sides of said tissues, at least one of said strands extending through said passageway;
sliding said locking device along at least said one of said strands until said locking device is substantially juxtaposed to said organic tissues;
upon juxtaposition of said locking device to said organic tissues, locking said strands in a tightened closure configuration via said locking device; and
severing said strands on a side of said locking device opposite said organic tissues.

14. The method defined in claim 13, further comprising the steps of:
disposing a trocar sleeve in an abdominal wall of the patient; and
moving a portion of said suture through said trocar sleeve and into an abdominal cavity of the patient, said organic tissues being located in said abdominal cavity, said step of moving being implemented prior to said step of passing.

15. The method defined in claim 14, further comprising the steps of:
upon completion of said step of passing, bringing an end section of said one of said strands back out through said trocar sleeve; and
upon completion of said step of bringing, inserting said one of said strands into said passageway so that said one of said strands extends through said passageway, said step of sliding being implemented after said step of inserting.

16. The method defined in claim 13 wherein both of said strands extend through said passageway prior to said step of sliding, said step of sliding including the step of sliding said locking device along at least said one of said strands until said locking device is substantially juxtaposed to said organic tissues, said step of locking being automatically implemented upon juxtaposition of said locking device to said organic tissues.

17. The method defined in claim 13 wherein said step of sliding includes the steps of:
providing an elongate instrument;
inserting a distal end portion of said elongate instrument through said trocar sleeve; and
pushing said locking device along said one of said strands by engaging said locking device with said distal end portion of said instrument.

18. The method defined in claim 17 wherein said instrument is provided at a distal tip of said distal end portion with a cutting edge, said step of severing including the step of manipulating said instrument and said strands from outside the patient so as to bring said strands at said locking device into contact with said edge.

19. The method defined in claim 17 wherein said instrument is provided at a distal tip of said distal end portion with an aperture smaller than said locking device, further comprising the step of passing said two strands through said aperture prior to insertion of said distal end portion of said instrument through said trocar sleeve.

20. The method defined in claim 13 wherein said locking device is provided with a pair of substantially parallel channels, said passageway constituting one of said channels, each of said channels being provided with means for preventing said suture from passing in a first predetermined direction along the respective channel while allowing the suture to slide relative to said body member in an opposite direction through the respective channel, further comprising the step of inserting said one of said strands through one of said channels in said opposite direction, said step of inserting being implemented prior to said step of sliding.

21. The method defined in claim 20, further comprising the step of additionally inserting another of said strands through another of said channels.

22. The method defined in claim 21 wherein said step of additionally inserting is implemented prior to said step of sliding.

23. A laparoscopic suturing method comprising the steps of:
disposing a trocar sleeve in an abdominal wall of a patient;
moving a portion of a suture through said trocar sleeve and into an abdominal cavity of the patient so that at least one end section of said suture remains outside the patient;
upon completion of said step of moving, passing said portion of said suture around organic tissues of the patient;
providing a locking device made of biocompatible material and having at least one passageway for receiving said suture, said locking device being further provided with means for preventing said suture from passing in a first predetermined direction along said passageway while allowing said suture to slide relative to said locking device in an opposite direction through said passageway;
sliding said locking device through said trocar sleeve and along at least one strand of said suture extending from said end section to said portion of said suture, said step of sliding being executed until said locking device is substantially juxtaposed to said organic tissues;
upon juxtaposition of said locking device to said organic tissues, locking said strands in a tightened closure configuration via said locking device; and
also upon juxtaposition of said locking device to said organic tissues, severing two strands of said suture on a side of said locking device opposite said organic tissues, said two strands including said one strand.

24. The method defined in claim 23, further comprising the steps of, upon completion of said step of passing, drawing a second end section of said suture back out through said trocar sleeve.

25. The method defined in claim 24 wherein both of the end sections extend through said passageway prior to said step of sliding, said step of sliding including the step of sliding said locking device along said two strands away from said end sections until said locking device is substantially juxtaposed to said organic tissues, said step of locking being automatically implemented upon juxtaposition of said locking device to said organic tissues.

26. The method defined in claim 23 wherein said step of sliding includes the steps of:
providing an elongate instrument;
inserting a distal end portion of said elongate instrument through said trocar sleeve; and
pushing said locking device along said one strand by engaging said locking device with said distal end portion of said instrument.

27. The method defined in claim 26 wherein said instrument is provided at a distal tip of said distal end portion with a cutting edge, said step of severing including the step of manipulating said instrument and said strands from outside the patient so as to bring said strands at said locking device into contact with said edge.

* * * * *